United States Patent [19]
Godowski et al.

[11] Patent Number: 5,175,000
[45] Date of Patent: Dec. 29, 1992

[54] FREE AMINE BENZOPHENANTHRIDINE ALKALOID COMPOSITIONS

[75] Inventors: Kenneth C. Godowski, Fort Collins; Ronald J. Harkrader, Westminster; Richard L. Dunn; Arthur J. Tipton, both of Fort Collins, all of Colo.

[73] Assignee: Vipont Pharmaceutical, Inc., Fort Collins, Colo.

[21] Appl. No.: 696,093

[22] Filed: May 6, 1991

Related U.S. Application Data

[63] Continuation-in-part of Ser. No. 400,561, Aug. 29, 1989, Pat. No. 5,013,553, which is a continuation-in-part of Ser. No. 68,251, Jun. 20, 1987, abandoned.

[51] Int. Cl.$^5$ .......................... A61K 7/26; A61K 9/00
[52] U.S. Cl. ..................................... 424/426; 424/43; 424/49; 424/58; 424/78.07; 424/423; 424/435; 424/451; 424/464; 424/195.1; 424/489; 514/902; 514/279; 514/280; 514/886; 514/887
[58] Field of Search .................... 424/426, 49, 58, 435

[56] References Cited

U.S. PATENT DOCUMENTS

| | | | |
|---|---|---|---|
| 3,754,332 | 8/1973 | Warren | 424/52 |
| 3,865,830 | 2/1975 | Turkevich et al. | 546/23 |
| 4,020,558 | 5/1977 | Cournut | 433/80 |
| 4,145,412 | 3/1979 | Ladanyi | 424/58 |
| 4,335,110 | 6/1982 | Collins | 424/49 |
| 4,376,115 | 3/1983 | McCrorey | 424/642 |
| 4,406,881 | 9/1983 | Ladanyi | 424/49 |
| 4,515,771 | 5/1985 | Fine | 424/52 |
| 4,517,172 | 5/1985 | Southard | 424/7.1 |
| 4,568,535 | 2/1986 | Loesche | 424/435 |
| 4,590,061 | 5/1986 | Southard | 424/7.1 |
| 4,599,228 | 7/1986 | Ladanyi | 424/52 |
| 4,683,133 | 7/1987 | Southard | 424/49 |
| 4,685,883 | 8/1987 | Jernberg | 433/215 |
| 4,689,216 | 8/1987 | Greene | 424/58 |
| 4,689,221 | 8/1987 | Kiyoshige et al. | 424/87 |
| 4,722,948 | 2/1988 | Sanderson | 523/115 |
| 4,735,945 | 4/1988 | Sakamoto et al. | 514/279 |
| 4,737,503 | 4/1988 | Sakamoto et al. | 514/279 |
| 4,764,377 | 8/1987 | Goodson | 424/435 |
| 4,767,861 | 8/1988 | Boulware | 546/41 |
| 4,769,452 | 9/1988 | Boulware | 540/476 |
| 4,780,320 | 10/1988 | Baker | 424/493 |
| 4,816,462 | 3/1989 | Nowicky | 514/279 |
| 4,818,533 | 4/1989 | Boulware et al. | 424/195.1 |
| 5,013,553 | 5/1991 | Southard et al. | 424/435 |

FOREIGN PATENT DOCUMENTS

| | | |
|---|---|---|
| 2755577 | 6/1980 | Fed. Rep. of Germany. |
| 2856577 | 6/1980 | Fed. Rep. of Germany. |
| 2042336 | 9/1980 | United Kingdom. |

OTHER PUBLICATIONS

E. F. Steinmetz, *Codex Vegetabilis* 277:1018 (1957).
W. C. Griffin, "Emulsions" in *Encyclopedia of Chem. Techn.*, volume 8, 2nd edition, John Wiley & Sons, Inc., New York, N.Y. (1965).
J. Slavik et al., *Plant Biochemistry* 62:10817-10818, "Alkaloids of Macleaya cordata" (1965).
N. G. Kiryakov, *Alkaloids* 67:Abstract No. 32849h (1967).
V. A. Chelombit'ko et al., *Pharmaceut. Chem. J.* 2:49-52 (English translation of *Khimiko-Farmatsevticheskii Zhurnal*) (1968).
D. A. Murav'eva et al., *Chem. Abstracts* 71:Abstract No. 109759w (1969).
D. A. Murav'eva et al., *Plant Biochemistry* 71:Abstract No. 120481v (1969).
S. A. Vichkanova et al., *Antibiotiki* 16:609-612 (1971) [English translation].
S. A. Vichkanova et al., *Microbial Biochem.* 75:95 (Abstract No. 95744f) (1971).
H. Grabarczyk et al., *Chem. Abstracts* 74:Abstract No. 95419h (1971).
S. A. Vichkanova et al., *Antibiotiki* 1:902 (1973) [English translation].
G. A. Maslova, *Chem. Abstracts* 81:Abstract No. 74303v (1974).
A. G. Kodash et al., *Biochem.* 83:Abstract No. 40240y (1974).
G. A. Maslova, *All–Union Scientific–Research Institute of Medical Plants* 2:261-262 (English translation of Khymiya Prirodnykh Soedinenii) (1974).
O. E. Lasskaya et al., *Chem. Abstracts* 87:Abstract No. 206494u (1977).
V. Simanek et al., *Heterocycles* 6:475 (1977).
O. Lasskaya et al., *Chem. Abstracts* 87:288 (Abstract No. 87:206494u) (1977).
Shamma et al., "Isoquinoline Alkaloids Research," Plenum Publishers, New York, N.Y. (1978).
M. Caolo et al., Heterocycles 12:11-15 (1979).
E. Taborska et al., *Plant Biochem.* 93:Abstract No. 41549z (1980).
E. Taborska et al., *Collection Czechoslov. Chem. Commun.* 45:1301 (1980).
E. Forche et al., *Planta Medica* 42:137 (1981) (discussed below).
D. Walterova, et al., *Acta Univ. Palacki. Olomuc. Fac. Med.* 97:121-135 (1981).
I. E. Kopylova, *Pharmaceutical Anal.* 94:Abstract No. 162811h (1981).
J. Ulrichova et al. et al., *Acta Univ. Palacki. Olomuc. Fac. Med.* 106:31-36 (1984).
Cerna et al., "Isoquinoline Alkaloids," in *Local Periodontal Disease Thereapy*, pp. 159-162 (1984).
G. L. Southard et al., *JADA* 108:338 (1984).

(List continued on next page.)

*Primary Examiner*—Thurman K. Page
*Assistant Examiner*—James M. Spear
*Attorney, Agent, or Firm*—Merchant, Gould, Smith, Edell, Welter & Schmidt

[57] ABSTRACT

A pharmaceutical composition of a free amine benzophenanthridine alkaloid and a pharmaceutically acceptable carrier is disclosed. The composition is an antibacterial and antifungal agent.

19 Claims, No Drawings

OTHER PUBLICATIONS

J. Kovar et al., *Collect. Czech. Chem. Commun.* 51:2626 (1986).

R. R. Jones et al., *J. Natural Products* 49:1109-11 (1986).

G. L. Southard et al., *J. Clin. Periodontal* 14:315-319 (1987).

S. B. Mahato et al., *Chem. Astracts 109:412 (Abstract No. 109:79698j) (1988).*

E. D. Wolff et al., *J. Dent. Res.* 69:Abstract No. 611 (1990).

J. Dostal et al., *Collect. Czech. Chem. Commun. 55:2841-2871 (1990).*

K. C. Godowski et al., *J. Dent. Res.* 69:Abstract No. 1139 (1990).

D. Scott Harper et al., *J. Periodontal* 61:352-358 (1990).

Simanek, Chapter 4 in "The Alkaloids", vol. 26, Academic Press, 1985, at pp. 229-232.

FREE AMINE BENZOPHENANTHRIDINE ALKALOID COMPOSITIONS

CROSS-REFERENCE TO RELATED APPLICATIONS

This application is a continuation-in-part of U.S. Ser. No. 07/400,561, filed Aug. 29, 1989 now U.S. Pat. No. 5,013,553 which is a continuation-in-part of U.S. Ser. No. 07/068,251, filed Jun. 30, 1987; abandoned.

BACKGROUND OF THE INVENTION

It is well-known that benzophenanthridine alkaloids can act as topical contact antibacterial and antifungal agents. It is also known that such activity is produced in vivo by combination of the benzophenanthridine alkaloids with potentiating agents such as mineral or organic acid salts of zinc, tin, copper, iron, aluminum or other similar complex forming metal salts or organic compounds.

A benzophenanthridine alkaloid can have one of two possible structures for its quinoline nucleus: an iminium structure or a free amine structure. The pH of the medium containing the alkaloid as well as chemical modifications can cause the alkaloid to convert from the iminium structure to a free amine structure.

Current belief holds that the iminium structure of the alkaloid has the necessary configuration and ionicity for transport across microorganism membranes and for chemical interaction with the biological system. As a corollary, the free amine alkaloid is thought to be inactive as an antibacterial or antifungal agent.

It is also thought that the physical character of the free amine alkaloid may contribute to its lack of activity. The free amine alkaloid is often, but not always, substantially insoluble in aqueous media because of its hydrophobic structure. However, hydrophilic derivatives of the free amine alkaloid can be prepared and these derivatives have greater solubility in aqueous solutions.

Based upon the understanding of the biological activity of benzophenanthridine alkaloids as conveyed by the art, it is expected that these alkaloids would have no biological activity at an approximately neutral pH or above. The predominant structure of the alkaloid at this higher pH is the free amine. The biological activity, however, is believed to be associated with the iminium structure, which is the predominant structure at the lower pH. Consequently, it is surprising to find according to the present invention that the benzophenanthridine alkaloids have increased biological activity at such higher pH's and very little activity at lower pH's which cause the iminium structure to be predominant. Moreover, it is surprising to find that benzophenanthridine alkaloid derivatives having the free base structure are also biologically active.

It is an object of the invention, therefore, to develop systemic and local pharmaceutical compositions that contain the benzophenanthridine alkaloid as the free amine. A further object is the development of appropriate parameters to maintain the benzophenanthridine alkaloid as the free amine.

SUMMARY OF THE INVENTION

These and other objects are achieved by the present invention which is directed to a pharmaceutical composition of a free amine benzophenanthridine alkaloid or derivative thereof in combination with a pharmaceutically acceptable carrier. The pharmaceutical composition is formulated either for local or systemic administration. The invention is as well directed to derivatives of the free amine benzophenanthridine alkaloids which preferably are water-soluble. Among these derivatives are synthetically modified benzophenanthridine alkaloids and polymer products composed of a water-soluble polymer coupled to the free amine alkaloid or synthetically modified form thereof.

To have biological activity, the benzophenanthridine alkaloid is maintained as the free amine either by control of the pH of the carrier, permanent synthetic alteration of the alkaloid structure into the free amine or formation of a chemically equilibrated free amine. The physical form of the free amine benzophenanthridine alkaloid is either a particulate form which can be suspended in the carrier, or a soluble form dissolved in the carrier. It is preferred that the free amine alkaloid be soluble in aqueous or aqueous-organic media. Certain derivatives of the benzophenanthridine alkaloids that carry hydroxyl, amine, or similar groups have such increased water-solubility. An especially preferred water-soluble free amine alkaloid derivative is the polymer product formed by coupling the free amine alkaloid to a water-soluble polymer.

The pharmaceutical carrier constitutes a physiologically compatible aqueous, aqueous-organic or organic medium of aerosol, liquid or solid design for diluting and suspending the base form alkaloid and assuring appropriate delivery to the biological treatment site. The carrier may also include further components appropriate for the route of administration and kind of treatment sought. No matter which route is to be adopted, a preferred component of the pharmaceutical carrier will be at least one buffering agent for maintaining the composition at a basic pH. A topical composition will also contain components for maintaining a substantially stable formulation of base form alkaloid. A systemic composition will contain sterile carrier and preferably anti-agglomerating agents, especially when the composition is to be administered by an intravenous route.

Preferred forms of the composition include a topical ointment, gel, suspension, solution, lotion or similar pharmacological formulation for external topical administration; an orally administrable gel, suspension, solution, disintegratable tablet, pill or capsule or similar pharmacological formulation for administration to the gastrointestinal tract; an aerosol or spray for administration to the nasal nares and lung; and an injectable gel, suspension, solution or similar pharmacological formulation for systemic administration. The routes of administration correlate with the biological site to be treated.

The invention also is directed to a method for treatment of a bacterial or fungal infection of a patient by administration to the patient of an effective amount of an appropriately selected version of the foregoing pharmaceutical composition. Topical administration of the liquid, gel or ointment applies to skin infections. Oral administration of the liquid or tablet form composition applies to infections of the GI tract. Nasal administration of the aerosol composition applies to localized external surface infections of the nasal cavity and lung. Venous, intramuscular or other systemic administration of the liquid composition applies to systemic infections. For systemic or other administration where the pharmaceutical composition will be diluted with physiological fluids, the benzophenanthridine alkaloid selected for the composition will have or will be modified to have a pKa that causes it to adopt the free amine structure at the pH of the physiological fluid.

DETAILED DESCRIPTION OF THE INVENTION

It has recently been discovered that benzophenanthridine alkaloids having the free amine structure exhibit antifungal and antibacterial activities in vitro and in vivo. Although it is not meant to be a limitation of this invention, it is believed that within the appropriate parameters, the free amine and not the iminium structure of the benzophenanthridine alkaloid possesses the predominant biological activity characteristic of this class of alkaloids. In retrospect, it appears that the iminium structure alone is not able to effectively inhibit or kill microorganisms. The iminium alkaloid apparently needs a metal salt potentiating agent to counteract the heretofore unknown biological deactivation caused by the iminium structure. In contrast, it has been found that such a metal salt potentiating agent is not necessary when the alkaloid is administered as the free amine.

The pharmaceutical composition is a combination of the free amine benzophenanthridine alkaloid, and a pharmaceutically acceptable, aqueous, aqueous-organic or organic diluent carrier. Depending on the particular carrier and free amine alkaloid selected, the free amine alkaloid or its derivative either can be dissolved in the carrier or can be suspended as particles in the carrier. For the solution embodiment of the pharmaceutical composition, it is preferred that the novel intermediate of the invention be used, that is, the polymeric product composed of a water-soluble polymer coupled with the free amine alkaloid as a pendent group or terminal group. If suspended as particles, it is believed that the solid particulate partially dissolves to establish an equilibrium between the solubilized free amine alkaloid and the solid particulate.

In addition to being a suspending or solubilizing medium for the free amine, the carrier can also incorporate further components such as buffering agents, suspending agents, anti-agglomerating agents and the like. The particular combination of carrier components incorporated will depend upon the route of administration chosen and the biological site to be treated. Those routes (and sites) include topical (skin, mucous membranes), systemic (muscle, venous, lymph, arteriole, peritoneal), oral (intestinal), aerosol or spray (lung and nasal) as well as cosmetic or shampoo (skin, hair), and oral care (mouth).

The character of the pharmaceutically acceptable carrier will vary according to the properties of the composition desired. For example, a topical formulation may be a stable suspension of the free amine alkaloid in a buffered aqueous lotion with a thickening agent such as a carboxymethylcellulose or it may be a buffered aqueous solution of the polymer product. Similarly, cosmetics and shampoos may be formulated to have greater fluidity than the topical lotions and gels. Systemic and aerosol or spray formulations may contain buffered aqueous carriers and the particle sizes in these instances will preferably be controlled so that formation of emboli is avoided. Alternatively, the systemic, aerosol or spray formulations may be buffered aqueous solutions of the water-soluble free amine alkaloid derivatives such as, for example, the glycerol or gluconic acid derivative or the polymer product. Disintegratable tablets, pills and capsules with a solid carrier such as milk sugar need not be buffered but will contain alkaloids that maintain the free amine structure at the physiological pH of the gut.

The benzophenanthridine alkaloids incorporated into the present invention constitute a class of alkaloids having a quinoline nucleus with two benzene rings fused at the 3,4 and 6,7 positions of the quinoline. Examples include sanguinarine, chelerythrine, and sanguilutine, chelilutine, chelirubine and sanguirubine. Many benzophenanthridine alkaloids are naturally occurring compounds present in certain plant tissues such as *Sanguinaria canadensis*, Macleaya, and Argemone. The individual benzophenanthridine alkaloids obtained from natural plant sources may be used in the present invention. Methods for the extraction, separation and purification of the various benzophenanthridine alkaloids from plant tissue are known. See, for example U.S. Pat. No. 4,818,533.

Derivatives, such as synthetically modified benzophenanthridine alkaloids, synthetically formed benzophenanthridine alkaloids, polymer products, and especially those derivatives which will maintain the free amine structure over a wide pH, may also be used. The synthetically modified benzophenanthridine alkaloids will preferably have substituents at the nitrogen and alpha carbon positions so that the free amine is rendered unable to convert to the iminium structure. Substituents for this purpose include hydroxyls, glycerols, glycols, alcohols, polyglycols, organic acids, organic amines and nucleophilic addition products obtained from the 8-oxyalkaloid having an amide moiety in place of the imine moiety. In addition, the hydrophilic and polar substituents serve to increase the water solubility of the alkaloid such that it can be formulated in solution. In the context of this invention, a benzophenanthridine alkaloid or a derivative thereof is water-soluble if it dissolves to the extent of at least 100 ppm, preferably 1,000 ppm, and more preferably 10,000 ppm in water or aqueous media. Synthetic methods for preparing modified benzophenanthridine alkaloids are given in "Isoquinoline Alkaloids Research" by Shamma and Monoit, Plenum Publishers, New York, N.Y. (1978), the disclosure of which is incorporated herein by reference.

A preferred water-soluble derivative of the free amine alkaloid is the polymer product formed by covalently coupling the free amine to a water-soluble polymer. In a first alternative, any polymer carrying nucleophilic groups such as hydroxyl, amine or sulfide groups that are free or pendent can be covalently coupled to the iminium moiety of the acidified benzophenanthridine alkaloid through reaction of the nucleophilic groups of the polymer and iminium moiety of the alkaloid, that is, reaction with the carbon alpha to the alkaloid nitrogen. This alpha carbon coupling will convert the iminium group to a free amine and couple the free amine alkaloid to the polymer through the iminium carbon. In a second alternative, a polymer can be covalently coupled either (1) by a known electrophilic substitution method to one of the masked hydroxyl groups present within the two methylenedioxy groups of the alkaloid or (2) by known nucleophilic substitution methods through the methylenedioxy group. This alternative is especially useful when the nitrogen of the alkaloid is derivatized such that it is already a free amine and cannot form an iminium group. These reactions are known in the art. Examples include electrophilic substitution of the carboxylic acid halide groups of a derivatized polyacrylic acid or a small organic acid compound and the alkaloid hydroxyls, or nucleophilic substitution of an organic compound carrying a carbanion, such as alkyl or aryl lithium or a grignard reagent, with (a) the methylenyl group of the alkaloid, or (b) the carbonyl group alpha to the nitrogen of an 8-oxybenzophenanthridine alkaloid (i.e., with the carbonyl of the amide moiety of the 8-oxyalkaloid).

Functional groups added at other positions around the alkaloid ring can also operate as sites for polymer coupling either by the nucleophilic or electrophilic methods outlined above. Known reactions for polymer coupling to side chains can be employed for this purpose. Examples include hydroxy (phenoxy) addition to epoxides, carboxylic acid halides or isocyanates; activated coupling between hydroxyls or amines and carboxylic acids such as with carbodiimide or carbonyldiimidazole reagents; and ring opening such as a pendent epoxide reaction with a carboxylic acid group.

Preferred examples of alkaloid coupling to polymers include the polymeric products formed by reaction of polyvinyl alcohol, polyethyleneimine or polyethylene glycol with the alkaloid having the iminium structure under basic aqueous conditions to bond the iminium carbon of the alkaloid to the pendent oxygen or nitrogen group of the polymer. This coupling produces the free amine alkaloid coupled to the polymer. The product is soluble in aqueous media.

Further preferred examples are the polymeric products formed by reaction of polyacrylic acid or a derivative thereof with the alkaloid derivative having the nitrogen permanently converted to the free amine, such as the 8-alkoxy derivative. The methylenedioxy group of the alkaloid derivative can be hydrolyzed and the resulting phenoxy-like compound coupled with polyacrylic acid through a carbodiimide coupling agent under less than stoichiometric conditions. The polyacrylic ester product is soluble in aqueous media.

The pharmaceutically acceptable carrier diluents and components incorporated according to the invention provide desirable characteristics to the pharmaceutical composition. These characteristics include dose measurement, dissolution, dilution, thickening, particle suspension, pH buffering, sweetening, stabilization against degradation, bulking, filling, emulsification, thixotropy, aerosolization, coloring, cleaning, antisorption, antiagglomeration, and the like. Appropriate liquid dilution media for the various routes include liquid compounds and compositions such as pharmaceutically compatible aqueous and/or organic diluents including lower ($C_1$ to $C_6$) aliphatic alcohols, polyglycols, polyvinylpyrrolidones and copolymers thereof, water, chlorinated liquids and oils. Appropriate gases for aerosol formation of the liquid compositions include carbon dioxide, nitrogen, air and noble element gases. Appropriate solid diluents for the oral administration route and for bolus injection include milk, sugar, talc, soluble gums and polysaccharides and solid inert fillers. Additional components for the various routes include waxes, anionic, nonionic, and cationic surfactants, emollients, emulsifiers, buffering systems such as carbonate and phosphate buffering systems, colors, thixotropic agents, gelation agents such as alginate, gum agar and kaolin clay, thickening agents, talcs, clays, sterilizing agents, polyhydroxy organic compounds, fillers, extenders, poly aliphatic or fatty alcohols or esters, absorption control agents, skin colorants, cosmetic ingredients and suspension stabilizers. These components provide such properties as gelation, suspension stability, pH control, sterility, bulking, appropriate tactile sensation, color and the like to the composition.

Selection of the carrier components will depend upon the treatment application for the pharmaceutical composition. Topical pharmaceutical compositions will include such components as emulsifiers, buffering agents, gelation agents and the like formulated for appropriate pH adjustment. Systemically administrable pharmaceutical compositions will include buffering agents and physiologically acceptable diluents but will typically not include waxes, oils, clays and other materials used as bulking agents and gelling agents in topical formulations. Application of the pharmaceutical composition to oral care will include such formulations as gels in the nature of toothpaste and mouth rinse concentrates. Cosmetics and shampoos will include buffering systems as well as suspending agents for the alkaloid particulates. In addition, tinting agents, texturizing agents, cleaning agents, and soaps will be included in cosmetics and shampoos as appropriate. Orally administrable pharmaceutical compositions for treatment of intestinal infections will include buffering agents, suspending agents and antiabsorption agents. Aerosol or spray formulations of the pharmaceutical compositions can incorporate the free amine alkaloid in combination with an aerosol and/or liquid diluents and the like for inhalation into the lungs. A preferable aerosol is a gas-solid combination of an inert gas carrier with the alkaloid particulate material. A water dispersing agent optionally buffered with a buffering system may also be included.

The pharmaceutical compositions may be prepared by known methods. Recipes and formulations for topical ointments, systemically administrable suspensions or solutions, disintegratable tablets, pills and capsules, cosmetics, shampoos, inhalers and oral care gels are known to those of skill in the art. See for example, W. C. Griffin, "Emulsions," Encyclopedia of Chemical Technology Vol. 8, 2nd ed. John Wiley & Sons, Inc., New York, N.Y. 1965 the disclosure of which is incorporated herein by reference. In a typical process for preparing the pharmaceutical compositions, the basic components for the pharmaceutical carrier such as diluents, a buffering system, surfactants, extenders and the like are first combined together and then an appropriate amount of the alkaloid material is added under shear stirring conditions to form the composition. Metering the appropriate amounts of the composition into containers designed for the chosen administration completes the process for preparation of the pharmaceutical compositions.

If the free amine alkaloid is to be dissolved in the formulations, it can be combined in concentrated form and then diluted to the appropriate dosage level. Alternatively, it can be directly compounded at the appropriate dosage level by dissolution in the carrier diluent or solvent followed by addition of other carrier components.

If the free amine alkaloid is to be used as a particulate in the formulations, it can be prepared by a number of methods. Grinding, milling, ball rolling, grating, pressing, mashing, dicing, spray drying and other similar methods for particle size reduction can be applied to large particles of the alkaloid as the free amine. Screening will appropriately select the desired maximum size of the alkaloid particles for inclusion in the pharmaceutical compositions. Double screening with maximum and minimum sizes can also be applied if appropriate.

Controlled particle formation from a dissolved solution of the alkaloid will also produce the desired particulate. For example, under certain conditions, alkaloid particles of controlled sizes can be precipitated from aqueous medium. The alkaloid is dissolved in an aqueous medium under acidic conditions, the medium is neutralized to provide slightly basic conditions and a precipitating amount of alcohol is slowly added. By controlling the temperature of the precipitating medium, the rate of precipitation and the agitation of the precipitating medium, the particulate size can be controlled within the appropriate parameters for particle size according to the invention. Generally, rapid cooling, a moderate concentration of dissolved alkaloid and rapid stirring will tend to produce particles in the lower portion of the size range. A preferred method for forming the alkaloid particles is provided in the following examples section.

The pharmaceutical compositions of the present invention are useful for the treatment of topical, systemic and site specific infections of gram positive and gram negative bacteria, fungi, mycoplasma, spirochetes, mycobacteria, rickettsia and chlamydia. The free amine benzophenanthridine alkaloids possess a broad spectrum anti-infective activity. Gram negative and gram positive infections of bacteria such as those causing pneumonia, rickettsial diseases, chlamydial diseases, streptococcal diseases, staphylococcal diseases, neisseria diseases, clostridial diseases, anaerobic bacterial diseases, salmonella diseases as well as sporulate borne disease, leptospiral disease, and treponemal disease.

Administration of the pharmaceutical composition of the present invention will generally follow the instructions and directions of an attending physician upon whose wisdom the ultimate choice of route of administration and dosage level will be based. Topical treatment of bacterial or fungal infected skin, mucous membrane and other epithelial infections can be accomplished by application of at least about 0.1 milligrams of free amine alkaloid per square centimeter of surface treated. Preferably, the application rate will be from about 0.2 milligrams to about 50 milligrams per square centimeter of surface area treated. Especially preferred dosages include about 5 mg to about 10 mg per square centimeter of surface area treated.

For systemic use, the routes of administration include intraperitoneal, intravenous, or any similar route that delivers the pharmaceutical composition to the appropriate body fluids. To treat bacterial infections, at least about 1 milligram of free amine alkaloid per kilogram of body weight of the patient will be administered from 2 to about 4 times per day. Preferably the amount of free amine alkaloid administered per kilogram of patient body weight will be from about 2 to 5 mg. For systemic fungal infections, at least about 1 milligram per kilogram of patient body weight will be administered approximately 2 to 4 times per day. Mycoplasma will be effectively treated by administration of at least about 2 milligrams per kilogram of patient body weight 2 to about 4 times per day.

The systemic administration such as by intravenous, arterial, intramuscular or subcutaneous delivery may be accomplished in a continuous manner through a slow drip or other periodic controlled or intermittent mode of introduction such as by injection. The dosage levels will cause blood levels of the alkaloid of approximately at least about 1 milligram per liter of blood. Preferably a water or body fluid soluble free amine alkaloid is used in such compositions for systemic administration.

Treatment of microbial and fungal infections on internal surfaces in contact with the outside environment, i.e., the epithelial tissue of the lungs or the gastrointestinal tract can be accomplished by administration of at least about 1 milligram of the alkaloid per kilogram of patient body weight from 2 to about 4 times per day.

For oral treatment of infections of the gastrointestinal tract, effective administration can be obtained by application of an elixir, a drench, a suspension, a rinse, a gel, a tablet, a pill or a capsule formulated to release up to about 50 mg of free amine alkaloid per dose with up to about 3 doses per day. These formulations will preferably include an antiabsorption agent to facilitate maintenance of the free amine alkaloid within the gut.

Control of the dosage for inhalator administration to the lungs can be accomplished by the combination of the aerosol gas, and pharmaceutically acceptable diluents such as water and a buffering system. The inhalator can be designed according to known methods to administer an appropriate volume of the composition for treatment of inner lung surfaces. Typically an amount of at least about 1 milligram of free amine alkaloid per kilogram of patient body weight for 2 to about 4 times per day by inhalator administration may be made.

Generally, if the pharmaceutical composition contains the free base alkaloid as a particulate solid, the particles will have sizes within a range for appropriate function of the intended treatment. For example, a topical suspension may contain particles small enough to deliver an extremely large surface area but not so small that they are difficult to manipulate during formulation. A systemic suspension may contain particles within a controlled size range so that emboli are avoided. A gastrointestinal suspension may contain large particles relative to the systemic suspension so that GI absorption is minimized. It will be understood, therefore, that a particle size range will vary according to the particular purpose for which the free base alkaloid is used. Generally, however, particles within a range of from about 0.01 micron to about 10 mm will be appropriate for these purposes. The lower end of this range is preferred for those uses most appropriately associated with a high surface area of particulate solid. Such instances would include effective topical, systemic and inhalator administration. The upper end of this range is preferred for those uses most appropriately associated with a need to minimize absorption. Such instances would include administration for gastrointestinal treatment and for sustained release by intramuscular, subcutaneous or similar routes. Further, if the particulate size of the free amine alkaloid is to be used for pharmaceutical compositions in systemic or inhalator administration, it is preferred that a particle size of no more than about 3 microns be used in this route of administration. This upper particle size limitation will avoid the possibility of the formation of internal emboli.

The free amine alkaloid as a particulate solid may also be directly implanted as a bolus, disintegratable tablet or injectable suspension, gel and the like into specific sites of the human or animal patient. This procedure is useful for isolated tissue infections. Preferably a moderately water-soluble free amine alkaloid is used in this instance so that systemic transport is minimized. It is also useful for sustained release of small amounts of the free amine alkaloid which results from the embodiment having a low solubility in body fluids. Periodontal diseases, diseases of the liver, lymphatic diseases, and diseases of organs that are not amply bathed in body fluids or blood can be treated according to this method of administration.

Relative to the current understanding about the activity of benzophenanthridine alkaloids conveyed in the literature, it is surprising to discover that the free amine benzophenanthridine alkaloids according to the present invention have significant antibacterial and antifungal activities. Time-kill tests using *Escherichia coli, Enterococcus faecalis, Bacillus cereus, Staphylococcus aureus* and *Candida albicans* as test microorganisms have demonstrated that the free base alkaloids were bactericidal and fungicidal. These tests have demonstrated that the free amine benzophenanthridine alkaloids exhibit antimicrobial activity against both Gram-positive and Gram-negative bacteria as well as antibiotic-resistant bacteria and against fungi.

Agar diffusion tests have also shown that free amine alkaloids inhibit anaerobic bacteria such as *Propionibacterium acnes*. Accordingly, the free amine benzophenanthridine alkaloids are suitable broad spectrum antimicrobics for systemic and topical treatment of infectious diseases. In bacterial and fungal assays for growth inhibition and cell death, it has been found that the free amine benzophenanthridine alkaloids effectively control microorganism growth and the like without the need to include metal salts. Data and results supportive of these indications are provided in the following examples section.

The following examples further illustrate the characteristics and properties of the present invention. The examples provide several preferred embodiments of the pharmaceutical compositions, the full parameters of which have been fully discussed.

EXAMPLE 1

Method of Manufacture of Free Amine Benzophenanthridine Alkaloid Derivatives with Low Water Solubilities This example illustrates a method for the controlled manufacture of a free amine benzophenanthridine alkaloid derivatives with limited water solubilities. The production of 8-ethoxydihydrosanguinarine is given. The method can be applied to any alkaloid of this class.

Sanguinarine chloride is converted to 8-ethoxydihydrosanguinarine by a precipitation procedure. The yield of 8-ethoxydihydrosanguinarine is 60-75%.

About 20.0 g of sanguinarine chloride is combined with about 3.3 L of ethanol to provide a concentration of about 6 g sanguinarine chloride/liter of ethanol. The solution is heated to about 65° C. for 30 minutes with overhead stirring at about 400 rpm. The hot solution is filtered under vacuum through filter paper and about 370 ml of a 2% sodium hydroxide/ethanol solution is added to provide about 18.5 ml of 2% sodium hydroxide/ethanol per g of sanguinarine chloride. The resulting solution is stirred for about 15 minutes, the solution is allowed to cool to room temperature and let stand for 16-24 hours for precipitate formation. The precipitate is collected by vacuum filtration and dried for 12-24 hours in a drying oven at 40° C. The crystals are analyzed for 8-ethoxydihydrosanguinarine purity by infrared spectroscopy specification.

This process can also be applied to chelerythrine, macarpine, chelilutine, chelirubine, and sanguilutine as well as $C_1$-$C_3$ alkyl, halogen, amide, hydroxy and alkoxy substituted derivatives thereof. The 8-substituted base forms of benzophenanthridine alkaloids having a $C_1$-$C_6$ alkoxy or hydroxy group at the 8 position can be prepared by substituting the appropriate alcohol (or water) for the ethanol in the foregoing method.

Method of Manufacture of Starting Material

The starting materials are isoquinoline alkaloids that belong to the benzophenanthridine class. They are of botanical origin and can be obtained from sources including various species in the Papaveraceae, Fumariaceae and Rutaceae families. Preferably Macleaya from the Papaveraceae family can be used. Macleaya, for example, contains sanguinarine at sufficiently high levels to use isolation techniques for commercial extraction and purification of sanguinarine chloride (SaCl). The isolated sanguinarine chloride is converted to a base form using hydroxide and alcohol.

The methods for isolation and purification of the various species of the benzophenanthridine alkaloid class may be found in *Planta Media*, 42, 137, 1981 (E. Foiche and B. Frantz) the disclosure of which is incorporated herein by reference. Substituted derivatives may be synthesized according to the methods given in V. Simenak and V. Preininger, *Heterocycles*, 6, 475, 1977 the disclosure of which is incorporated herein by reference.

EXAMPLE 2

Liquid Media Formulations

Liquid formulations with varying amounts of 8-hydroxydihydrosanguinarine chloride or 8-ethoxydihydrosanguinarine were prepared as follows.

All formulations had the same following lotion base.

Lotion Base

| Ingredient | Weight % |
|---|---|
| RO/DI Water containing 400 Il of 1M NaOH per 100 g of formulation | 59.00 |
| Ethanol | 10.00 |
| Propylene Glycol | 1.00 |
| PEG 400 Monostearate | 30.00 |

Because 8-hydroxydihydrosanguinarine (SaOH) and 8-ethoxydihydrosanguinarine are fairly insoluble in water, they were added to the formulation after all other ingredients were combined. These formulations at 0.1-1.0% by weight SaOET or SaOH are dispersions and are at about pH 8 as opposed to about pH 4 for sanguinarine chloride formulations.

Other formulations of injectable suspensions, gels, shampoos and the like can be prepared by first combining the formulation medium with the other ingredients and then mixing in the free amine benzophenanthridine alkaloid. The following formulations can be prepared following this protocol and using the amounts of ingredients indicated.

| Ingredient | Weight % |
|---|---|
| Isopropyl isostearate | 6.00 |
| Propylene glycol | 5.00 |
| PEG-100 stearate | 5.00 |
| Carbomer 941 | 1.00 |
| Deionized water | 71.10 |
| Cetyl alcohol | .30 |
| 8-ethoxydihydrosanguinarine | 2.00 |
| 40% Potassium hydroxide | 1.00 |
| Fragrance | .30 |

-continued

| | |
|---|---|
| Methylparaben | .20 |
| Propylparaben | .10 |
| Diisopropyl dimerate | 8.00 |
| | 100.00 |

Toothpaste Formulation

This formulation contains finely divided free base alkaloid (1 to 100 microns) suspended in a gel.

| | |
|---|---|
| Hydrated silica abrasives | 25.00 |
| Sorbitol 70% solution | 50.00 |
| Glycerin | 18.00 |
| Sodium lauryl sulfate | 1.20 |
| Sodium monofluorophosphate | .80 |
| Flavor | 1.00 |
| Sodium saccharin | .30 |
| Titanium Dioxide | 1.00 |
| 8-hydroxydihydrosanguinarine | .10 |
| Sodium phosphate monobasic | 1.50 |
| Sodium phosphate dibasic | .60 |
| Water | 1.50 |
| | 100.00 |

Injectable Suspension

In this injectable suspension, the free amine alkaloid has a particle size within the range from about 0.1 to 2 microns. The suspension is agitated to thoroughly mix it immediately before injection.

| | |
|---|---|
| 8-Hydroxydihydrosanguinarine | 2.00 |
| 5% Dextrose USP | 5.00 |
| Sodium Bicarbonate | .10 |
| Water for Injection USP | 92.90 |
| | 100.00 |

Antifungal Shampoo

| | |
|---|---|
| Sodium lauryl sulfate | 5.00 |
| Triethanolamine | 5.00 |
| Lauryl betaine | 6.00 |
| Ethylene glycol stearate | 2.00 |
| Polyethylene glycol | 5.00 |
| 8-hydroxydihydrochelerythrine | 2.00 |
| Ammonium hydroxide | .10 |
| Fragrance | .30 |
| Water | 69.60 |
| | 100.00 |

Nonabsorbable Oral Formulation

The free amine alkaloid can be formulated as particles from 0.01 to 5 mm in size.

| | |
|---|---|
| 8-Hydroxydihydrosanguinarine | 0.020 |
| Sodium saccharin | 0.2 |
| Carboxymethylcellulose | 0.500 |
| Glycerin | 3.000 |
| Ethyl Alcohol | 10.000 |
| Flavor | 1.000 |
| Sodium Citrate | 0.200 |
| 40% Potassium hydroxide | 0.100 |
| Water | 84.98 |
| | 100.00 |

Inhalator Formulation

After mixing, the composition is added to a pumpable misting inhalator device. The particulate free amine alkaloid has a particle size of from 0.1 to 1 micron.

| | |
|---|---|
| 8-Ethoxydihydrosanguinarine | 0.08 |
| Sorbitan Trioleate | 2.10 |
| Trichloromonofluoromethane NF | 2.20 |
| Dichlorotetrafluoroethane NF | 2.20 |
| Dichlorodifluoromethane | 5.20 |
| 20% Sodium Hydroxide | 0.20 |
| Water USP | 88.02 |
| | 100.00 |

EXAMPLE 3

Preparation of Polyvinyl Alcohol-Alkaloid Product

To 4.60 g of a 4% polyvinyl alcohol (pVOH, mw is) solution in water was added 0.0243 g sanguinarine chloride SaCl with stirring. A portion (0.35 ml) of 10.0N NaOH was added. The reaction mixture was a solution, was almost colorless with a slight tan/orange color. After stirring 10 ml $H_2O$ was added in two small aliquots.

The reaction material was filtered through glass wool two times to produce a slightly cloudy solution. The solution was loaded in a syringe of a small volume (1.2 ml) and filtered through a 0.471 syringe filter. The resulting solution was clear and colorless. The colorless nature of the solution was an indication that if the alkaloid was present it had converted to the free amine structure. An aliquot of the clear solution (1 ml) was taken and measured by UV spectrophotometry. The UV spectrum was off-scale relative to the standard curve for sanguinarine chloride. To the analyzed aliquot was added 1 drop 6N HCl which produced a very orange cloudy solution. This reaction indicated cleavage of the alkaloid from the polymer. The acidified sample (1 ml) was diluted with 9 ml $H_2O$ to yield a clear, orange solution. The UV spectrum of the sample was taken but was too high to analyzed. The sample (2 ml) was diluted with 2 ml $H_2O$ and the UV spectrum again taken. Based upon the extinction coefficient for sanguinarine, this sample contained 32.4 ppm of sanguinarine, equivalent to 2592 ppm of the original polymer-alkaloid compound in water.

EXAMPLE 4

Preparation of Polyethylene Glycol-Alkaloid Product

Polymer products of polyethylene glycol (PEG) of various molecular weights were coupled to Sanguinarine chloride (SaCl) (iminium form) by reaction under basic aqueous conditions. Aqueous solutions of the polyethylene glycol, sanguinarine chloride and sodium hydroxide were prepared. Appropriate amounts of theses aqueous solutions were combined such that the sanguinarine chloride was present in substantially less than a stoichiometric amount. The combined solution was stirred at room temperature for a short time (about 5 to 10 minutes). The combined solution was analyzed by ultraviolet spectrometry to determine the portion of sanguinarine incorporated.

TABLE 1

| | SaCl ml* | PEG mw | PEG amt | NaOH amt (0.01N) |
|---|---|---|---|---|
| 1. | 25 | 600 | 0.25 g | 2 drops |

TABLE 1-continued

|   | SaCl ml* | PEG mw | PEG amt | NaOH amt (0.01N) |
|---|---|---|---|---|
| 2. | 25 | 1,500 | 0.25 g | 2 drops |
| 3. | 25 | 3,400 | 0.25 g | 2 drops |
| 4. | 25 | 10,000 | 0.25 g | 2 drops |
| 5. | 25 | 4 million | 0.25 g | 2 drops |

*The sanguinarine chloride was present at a concentration of 0.2 molar or 2,000 ppm.

Runs 1, 4 and 5 appeared to be clear with no precipitate. Runs 2 and 3 contained much precipitate. After filtration, UV spectra were taken which indicated incorporation of the sanguinarine into the polyethylene glycol structure as a terminal group bound to the terminal hydroxyl of the glycol. The resulting polymer product was completely water soluble in all instances.

EXAMPLE 5

Biological Assay of Antibacterial or Antifungal Activity of Base Forms of Sanguinarine The traditional time kill assay was modified into a highly sensitive test method to detect the bactericidal activity of a test agent. The time kill assay was used to study the mode of action of the following benzophenanthridine alkaloids: sanguinarine chloride (SaCl), 8-hydroxydihydrosanguinarine (SaOH) and 8-ethoxydihydrosanguinarine (SaOET) and the polyethylene glycol sanguinarine polymer (PEG-Sa) at different pHs.

The time-kill procedure used is briefly described as follows. The test microorganism was suspended in phosphate buffered saline (PBS) containing the test agent at the proper pH. Temperature was maintained at 37½C. At designated timepoints aliquots of test solution were removed and spread plated to agar plates composed of the appropriate growth media. The plates were then incubated and the colony forming units/mL (CFU/mL) were enumerated.

Test agents were assayed at concentrations roughly twice the minimum inhibitory concentration (MIC) of SaCl for the test microorganism. PBS without test agent served as negative control. Bactericidal or fungicidal activity was demonstrated by a decrease in the mean value CFU/mL over time.

Table 2 shows the bacterial activity of SaCl, SaOET, and SaOH at pH 8 compared to pH 6. Results demonstrate that at pH 8, where SaCl converts to the free amine, there is clearly bactericidal activity due to SaCl, SaOH and SaOET while at pH 6 no activity is detected.

Table 3 demonstrates the bactericidal activity of SaCl and chelerythrine chloride (ChCl) at pH 6, 7 and 8. Results indicate that SaCl antibacterial activity increased with increasing pH, as does ChCl using the Gram-positive bacteria, E. faecalis. SaCl is more active than ChCl, at each corresponding pH. This may be related to the fact that ChCl has a higher pKa than SaCl. More iminium form is present with ChCl than with SaCl at the pHs tested perhaps explaining the lesser activity of ChCl.

TABLE 2

Surviving E. coli ATCC 25922 at 180 minutes after exposure to various agents at pH 6 and 8.
Agent concentration = 30 lg/mL.

| AGENT | CFU/mL |
|---|---|
| Phosphate buffered saline, pH 6 | 1820 |
| SaCl, pH 6 | 1760 |
| SaOET, pH 6 | 1760 |
| SaOH, pH 6 | 1760 |

TABLE 2-continued

Surviving E. coli ATCC 25922 at 180 minutes after exposure to various agents at pH 6 and 8.
Agent concentration = 30 lg/mL.

| AGENT | CFU/mL |
|---|---|
| Phosphate buffered saline, pH 8 | 1610 |
| SaCl, pH 8 | 0 |
| SaOET, pH 8 | 0 |
| SaOH, pH 8 | 650 |

The use of E. coli in the time-kill assay focused on the differences in bacteriocidal activity of SaCl, SaOH and SaOET at different pHs. Results obtained indicate that the bactericidal activity of SaCl was apparently dependent on the relationship of test solution pH and the $pK_a$ of SaCl. HPLC analysis of sanguinarine iminium ion versus pH in a different test system has shown 87.9%, 41.1% 5.0% and 1.5% iminium to be present at pH=6.0, 6.6, 7.0 and 7.6 respectively.

TABLE 3

Surviving E. faecalis ATCC 29212 at 24 hours after exposure to SaCl, ChCl at pH 6, 7, and 8.
Agent Concentration = 4 lg/mL

| AGENT | CFU/mL ( × 10³) |
|---|---|
| Phosphate buffered saline, pH 6 | 873 |
| SaCl, pH 6 | 630 |
| ChCl, pH 6 | 783 |
| Phosphate buffered saline, pH 7 | 767 |
| SaCl, pH 7 | 211 |
| ChCl, pH 7 | 473 |
| Phosphate buffered saline, pH 8 | 717 |
| SaCl, pH 8 | 0.4 |
| ChCl, pH 8 | 239 |

Table 4 demonstrates the antifungal activity of SaCl increases with increasing pH using the yeast C. albicans as indicator microorganism.

Table 4 indicates that the water-soluble polymeric free amine is also antibacterial at pH 8.

In summary, the bactericidal activity of SaCl, SaOET, and SaOH was enhanced with increasing pH using the Gram-negative bacteria E. coli as test microorganism. The bacteriocidal activity of both SaCl and ChCl was enhanced with increasing pH, using the Gram-positive bacteria E. faecalis as test microorganism. The fungicidal activity of SaCl was enhanced with increasing pH, using the yeast C. albicans as test microorganism. The water-soluble polymeric (PEG) free amine form of sanguinarine was bactericidal at pH 8 using E. coli as test microorganism. The free amine form of sanguinarine appeared more bactericidal and fungicidal than the iminium form of sanguinarine at the pH ranges tested.

TABLE 4

Surviving C. albicans ATCC 14053 at 120 minutes after exposure to SaCl at pH 6, 7 and 8.
Agent Concentration = 2.7 lg/mL.

| AGENT | CFU/mL |
|---|---|
| Phosphate buffered saline, pH 6 | 3603 |
| SaCl, pH 6 | 3863 |
| Phosphate buffered saline, pH 7 | 3593 |
| SaCl, pH 7 | 2423 |
| Phosphate buffered saline, pH 8 | 3713 |
| SaCl, pH 8 | 0 |

TABLE 5

Surviving *E. coli* ATCC 25922 at
360 minutes after exposure to SaCl and water
soluble base form Sa at pH 8.
Agent concentration = 30 Ig/mL.

| AGENT | CFU/mL |
|---|---|
| Phosphate buffered saline | 2480 |
| SaCl | 0 |
| Water soluble polymer-sanguinarine product of Example 4 (PEG mw is 4 million) | 15 |

What is claimed is:

1. A method for the treatment of a bacterial or fungal infection in a patient comprising:
    administering to the patient an affective amount of a pharmaceutical composition of benzophenanthridine alkaloid in a free amine form or a derivative thereof in a free amine form and a pharmaceutically acceptable carrier of an aqueous medium, an aqueous-organic medium or an organic material; wherein,
    the free amine form of the benzophenanthridine alkaloid or derivative is established by maintaining the pH of the carrier at least at 6.8, by permanent synthetic alteration of the benzophenanthridine alkaloid structure, or by chemical equilibration of the benzophenanthridine alkaloid;
    the derivative is selected from the group consisting of a synthetically modified naturally occurring benzophenanthridine alkaloid, a synthetically formed benzophenanthridine alkaloid, a benzophenanthridine alkaloid substituted at the nitrogen by a group which renders the benzophenanthridine alkaloid unable to adopt an imminium form, a benzophenanthridine alkaloid substituted at the carbon alpha to the nitrogen by a group which renders the benzophenanthridine alkaloid unable to adopt an imminium form, a benzophenanthridine alkaloid substituted by hydrophilic or polar groups that increase the water solubility of the benzophenanthridine alkaloid, and any combination thereof.

2. A method for the treatment of a bacterial or fungal infection in a patient comprising administering to the patient an effective amount of a pharmaceutical composition of a water-soluble benzophenanthridine alkaloid in a free amine form or a derivative thereof in a free amine form and a pharmaceutically acceptable carrier of an aqueous medium, an aqueous-organic medium or an organic material; wherein,
    the free amine form of the benzophenanthridine alkaloid or derivative is established by maintaining the pH of the carrier at least at 6.8, by permanent synthetic alteration of the benzophenanthridine alkaloid structure, or by chemical equilibration of the benzophenanthridine alkaloid;
    the derivative is selected from the group consisting of a synthetically modified naturally occurring benzophenanthridine alkaloid, a synthetically formed benzophenanthridine alkaloid, a benzophenanthridine alkaloid substituted at the nitrogen by a group which renders the benzophenanthridine alkaloid unable to adopt an imminium form, a benzophenanthridine alkaloid substituted at the carbon alpha to the nitrogen by a group which renders the benzophenanthridine alkaloid unable to adopt an imminium structure, a benzophenanthridine alkaloid substituted by hydrophilic or polar groups that increase the water solubility of the benzophenanthridine alkaloid, and any combination thereof;

3. A method according to claim 1 wherein the composition is formulated as an aerosol or spray.

4. A method according to claim 1 wherein the composition is formulated as a topical ointment.

5. A method according to claim 1 wherein the free amine benzophenanthridine alkaloid is in a particulate form with particles having an average particle diameter of no more than about 10 mm.

6. A method according to claim 1 wherein the free amine benzophenanthridine alkaloid is a purified, naturally occurring benzophenanthridine alkaloid.

7. A method according to claim 1 wherein the pharmaceutical composition contains a free amine benzophenanthridine alkaloid derivative.

8. A method according to claim 7 wherein the derivative is a synthetically altered benzophenanthridine alkaloid.

9. A method according to claim 8 wherein the synthetically modified benzophenanthridine alkaloid is modified at the carbon alpha to the nitrogen or at the dioxymethylene group, or is a glycerol, gluconic acid or organic carboxylic acid reaction product.

10. A method according to claim 1 wherein the benzophenanthridine alkaloid or derivative is covalently bonded to a water-soluble polymer.

11. A method according to claim 7 wherein the derivative is water-soluble.

12. A method according to claim 1 wherein the carrier includes one or more of oils, emollients, waxes, buffers, colorants, emulsifiers, surfactants, polyhydroxy organic compounds, fillers, extenders, water, aliphatic and fatty alcohols, talcs, poly fatty esters, bulking agents, antisorption agents, anti-agglomeration agents, polyvinylpyrrolidones, sweeteners, cleaning agents, thickening agents, gums, milk solids, sugars, alginates, suspending agents, inert gases, starches, polysaccharides, clays, colorants, chlorinated liquids and degradation stabilizers.

13. A method according to claim 1 wherein the compositions is formulates as a solid disintegratable tablet, pill or capsule.

14. A polymer product comprising a water-soluble organic polymer having covalently bonded pendant or terminal groups of a benzophenanthridine alkaloid in a free amine form or a derivative thereof in a free amine form; wherein,
    the free amine form of the benzophenanthridine alkaloid or derivative is established by permanent synthetic alteration of the benzophenanthridine alkaloid structure, or by chemical eqiuilibration of the benzophenanthridine alkaloid;
    the derivative is selected from the group consisting of a synthetically modified naturally occurring benzophenanthridine alkaloid, a synthetically formed benzophenanthridine alkaloid, a benzophenanthridine alkaloid substituted at the nitrogen by a group which renders the benzophenanthridine alkaloid unable to adopt an imminium form, a benzophenanthridine alkaloid substituted at the carbon alpha to the nitrogen by a group which renders the benzophenanthridine alkaloid unable to adopt an imminium form, and any combination thereof.

15. A method according to claim 1 wherein the composition is formulated as an ointment, gel or lotion.

16. A method according to claim 1 wherein the composition is formulated as an injectable suspension.

17. A method according to claim 1 wherein the composition is a toothpaste or mouthwash.

18. A method according to claim 17 wherein the product is a toothpaste or mouthwash.

19. A method according to claim 18 wherein the product is a fluid material suitable for injection or implantation into or onto gingival tissue.

* * * * *